United States Patent [19]

Weinrotter et al.

[11] 3,984,471

[45] Oct. 5, 1976

[54] RECOVERY OF GUANIDINE CARBONATE FROM AQUEOUS SOLUTIONS

[75] Inventors: Ferdinand Weinrotter, Linz (Danube); Alfred Schmidt, Vienna; Karlheinz Wegleitner, Linz (Danube); Alfred Garber, Linz (Danube); Josef Herbert Hatzl, Linz (Danube); Rudolf Sykora, Linz-Dornach, all of Austria

[73] Assignee: Chemie Linz Aktiengesellschaft, Linz, Austria

[22] Filed: July 18, 1975

[21] Appl. No.: 597,008

[30] Foreign Application Priority Data

July 22, 1974  Germany............................ 2435167

[52] U.S. Cl............................................ 260/564 D
[51] Int. Cl.²...................................... C07C 129/02
[58] Field of Search................................ 260/564 D

[56] References Cited
FOREIGN PATENTS OR APPLICATIONS
2,234,732  1/1974  Germany ........................ 260/564 D

*Primary Examiner*—Gerald A. Schwartz
*Attorney, Agent, or Firm*—Wenderoth, Lind & Ponack

[57] ABSTRACT

Guanidine carbonate is isolated from dilute aqueous solutions containing guanidine, urea, pyrolysis products of urea, ammonia and carbon dioxide, by evaporation of the solution at a temperature of 80° to 130° C until a guanidine carbonate content of 20g/l and a pyrolysis products content of not more than 28g/l at 80° C or not more than 128° g/l at 30° C is achieved, without exceeding a heating time of 6 hours at the upper temperature limit, separation of the precipitated pyrolysis products, subsequent cooling to not more than 45° C, addition of ammonia to an ammonia content of 15 to 30 % by weight and separation of the precipitated guanidine carbonate.

7 Claims, No Drawings

RECOVERY OF GUANIDINE CARBONATE FROM AQUEOUS SOLUTIONS

This invention relates to a process for the isolation of guanidine carbonate from dilute aqueous solutions and particularly from mother liquors obtained from the catalytic preparation of melamine from urea or cyanic acid and ammonia.

The instability of guanidine or guanidine carbonate and urea in hot aqueous solutions has been known for some time. West German Offenlegungschrift No. 2,234,732 describes the working up of dilute aqueous solutions which contain guanidine, urea and the pyrolysis products thereof, such as melamine and several others, as well as ammonia and carbon dioxide, largely in the form of ammonium carbonate. According to this disclosure, guanidine is obtained in the form of its carbonate, in high yield and high purity, by evaporating the mother liquors obtained, at a temperature of not more than 80°C, in vacuo down to a small residual amount of water, precipitating the guanidine carbonate by addition of liquid ammonia and then purifying it merely by suspending the guanidine carbonate in liquid ammonia.

Furthermore, it is possible, using this prior process, at the same time to recover the urea present in the original mother liquor, largely without decomposition.

However, it is not always advantageous to use this method of isolating guanidine. For example, the amount of urea present may be relatively low, so that it is more economical to hydrolyse the urea as far as possible to ammonia and carbon dioxide and re-use these products, if appropriate, in the circulation of the original process.

If the process which produces the said aqueous solutions is carried out under normal pressure or slight excess pressure, attempts frequently may by made to work up the mother liquors under the same conditions, which is technically and economically substantially more advantageous than evaporation in vacuo. Finally, the extensive evaporation which is required for the purpose, and the large amounts of liquid ammonia, entail an expense which is only justified if the urea is to be regarded as a desired product.

It has now been found that it is possible, under quite specific process conditions, on the one hand to convert the urea partially or wholly, as desired, to ammonia and carbon dioxide by hydrolysis, and at the same time to dispense with the extensive evaporation of the mother liquor in vacuo. In this method, the amount of ammonia required is substantially less than in prior processes and the guanidine may be obtained from the evaporated mother liquors, in the form of its carbonate, in high purity and in yields which are economical. This proves possible if a controlled selective decomposition of the urea is carried out in the mixture under quite specific conditions, in which case, at the composition thus achieved, a relatively low concentration of ammonia suffices to precipitate the guanidine.

Accordingly, the present invention provides a process for isolating guanidine carbonate from a dilute aqueous solution which contains guanidine, urea and pyrolysis products thereof, ammonia and carbon dioxide, especially a mother liquor derived from the catalytic preparation of melamine from urea or cyanic acid and ammonia, which process comprises evaporating the solution at a temperature from 80° to 130° C until a content of guanidine carbonate of at least 20 g/l and a content of pyrolysis products of not more than 28 g/l, at an evaporation temperature of 80° C, or not more than 128 g/l, at an evaporation temperature of 130° C, is achieved, without exceeding a heating time of 6 hours at the upper limiting temperature, removing precipitated pyrolysis products, subsequently cooling the resulting solution to 45° C and below and adjusting the ammonia content of the solution to 15 to 30 % by weight by adding gaseous or liquid ammonia or a concentrated aqueous solution of ammonia, and separating the resulting precipitated guanidine carbonate, and, if desired washing the precipitate with aqueous ammonia.

In carrying out the process of the invention, heating to a temperature from 105° to 115° C is particularly advantageous, a slight excess pressure of up to 1.3 atmospheres then being necessary. Normally, a treatment time of 6 hours, as has been specified, with 130° C as the upper temperature limit, is not necessary to achieve the requisite decomposition rate. Usually, an evaporation time of 2 to 4 hours at 130° C is suitable. If the temperature is lowered, the heating time may be extended further, but at 110° C a time of 5 to 6 hours is quite sufficient for performing the process of the invention. At 80° C, the heating time may be extended yet further. Even at heating times of 10 hours no excessive decomposition of the guanidine carbonate present in the solution was observed.

After completion of the evaporation, it is necessary to cool the mixture at least to the point where the solubility of ammonia corresponds to the requisite minimum concentration of 15% by weight.

This is the case at a temperature of 45°C. However, under certain circumstances it is advisable to cool the mixture further down to ambient temperature since a higher ammonia concentration than 15% by weight favours the precipitation conditions. Even lower temperatures may be used, in which case it is necessary to ensure that the temperature is not taken below the solubility limit of the other materials present. An ammonia concentration of 20 to 25% by weight is preferred.

The ammonia may be introduced in any desired manner. It is preferred to introduce gaseous ammonia, on the one hand for economic reasons and on the other hand to avoid an excessive increase in volume, such as must be tolerated when adding aqueous ammonia. The introduction of gaseous ammonia makes it possible to carry out the evaporation stage as economically as possible. In such a case it frequently suffices to evaporate the mother liquor to about twice its concentration or to a water content of 80 to 80% in the solution.

After setting up the requisite ammonia concentration, the guanidine carbonate which precipitates is isolated, for which purpose the mixture may be either filtered or centrifuged.

The process may be carried out not only discontinuously but also, without any problems, continuously.

The following Example illustrates the invention and the manner in which it may be performed.

EXAMPLE

A melamine mother liquor has approximately the following composition by weight:

5%    of urea
1.75% of guanidine (calculated as the carbonate)

| | |
|---|---|
| 0.45% | of pyrolysis products (melamine and several others) |
| 11.1: | of ammonia |
| 8.5% | of carbon dioxide | remainder % water.

One tonne of this solution is evaporated at a temperature of 107°C and a pressure of 1.3 atmospheres over the course of 5 hours to one-sixth of its initial volume. A solution consisting of the following is obtained:

| | |
|---|---|
| 24.5 kg of urea | 12.75% |
| 15.6 kg of guanidine carbonate | 8.12% |
| 4.5 kg of pyrolysis products | 2.33% |
| 5.0 kg of ammonia | 2.60% |
| 142.4 kg of water | 74.20% |
| 192.0 kg | 100.00% |

Corresponding to this composition after evaporation it is calculated that relative to the concentration in the original solution, 51% decomposition of the urea and 11% decomposition of the guanidine carbonate has taken place.

The solution is cooled, whereupon 3.5 kg of pyrolysis products, especially melamine, precipitate. The precipitate is filtered off and washed with 3.5 kg of water.

The resulting solution has the following composition:

| | |
|---|---|
| 24.5 Kg of urea | 12.75% |
| 15.6 kg of guanidine carbonate | 8.12% |
| 1.0 kg of melamine | 0.53% |
| 5.0 kg of ammonia | 2.60% |
| 145.9 kg of water | 76.00% |
| 192.0 kg | 100.00% |

This solution is cooled to ambient temperature and ammonia is passed in until an ammonia concentration is 25% by weight is reached. Guanidine carbonate precipitates in an amount of 11.9 kg, corresponding to a yield of 68% relative to the melamine mother liquor, and in almost 99% purity. The precipitation itself takes place to a degree of 76.3%.

The solution which remains after separating off the guanidine carbonate has the following composition:

| |
|---|
| 24.5 Kg of urea |
| 3.7 kg of gunadine carbonate |

| | |
|---|---|
| 1.0 | kg of pyrolysis products (especially melamine) |
| 61.3 | kg of ammonia |
| 154.9 | kg of water |
| 245.4 | kg |

This solution may be returned into the usually continuously heated mother liquor evaporator. In doing so, for example, the urea is practically completely decomposed after 3 to 4 circulations under the stated conditions, whilst guanidine carbonate is hydrolysed only to a slight extent and the non-hydrolysed part is also isolated.

According to the above Example it is thus possible to isolate, as carbonate, a total of 86% of the guanidine present in the original melamine mother liquor.

What we claim is:

1. In a process for isolating guanidine carbonate from a dilute aqueous solution which contains guanidine, urea and pyrolysis products thereof, ammonia and carbon dioxide, the improvement which comprises evaporating the solution at a temperature from 80° to 130° C until a content of guanidine carbonate of at least 20 g/l and a content of pyrolysis products of not more than 28 g/l at evaporation temperature of 80° C, or not more than 128 g/l, at on evaporation temperature of 130° C, is achieved, whithout exceeding a heating time of 6 hours at the upper limiting temperature, filtering off precipitated pyrolysis products, subsequently cooling the resulting solution to 45° C and below and adjusting the ammonia content of the solution to 15 to 30 % by weight by adding gaseous or liquid ammonia or a concentrated aqueous solution of ammonia and separating the resulting precipitated carbonate.

2. A process according to claim 1, in which the starting dilute aqueous solution is a mother liquor from the catalytic preparation of melamine from urea or cyanic acid and ammonia.

3. A process according to claim 1, in which the evaporation temperature is from 105° to 115° C.

4. A process according to claim 1, in which the pressure during evaporation is from 1 to 1.3 atmospheres.

5. A process according to claim 1, in which the heating time at 130° C is 2 to 4 hours.

6. A process according to claim 1, in which the ammonia concentration is 20 to 25% by weight.

7. A process according to claim 1, in which the remaining solution which has been freed from precipitated guanidine carbonate, is recycled to the evaporation stage.

* * * * *